United States Patent [19]

Klein et al.

[11] 4,197,291

[45] Apr. 8, 1980

[54] HYDROLYTIC ENZYME MATERIAL

[75] Inventors: Gerold K. V. Klein, Merepoint Rd., Brunswick, Me. 04011; John C. Houck, Washington, D.C.

[73] Assignee: Gerold K. V. Klein, Brunswick, Me.

[21] Appl. No.: 887,607

[22] Filed: Mar. 17, 1978

Related U.S. Application Data

[63] Continuation of Ser. No. 678,695, Apr. 20, 1976, abandoned, which is a continuation-in-part of Ser. No. 489,254, Jul. 17, 1974, abandoned, which is a continuation of Ser. No. 431,622, Jan. 8, 1974, abandoned.

[51] Int. Cl.$^2$ .................. A61K 37/54; C07G 7/022
[52] U.S. Cl. .................................. 424/94; 435/195; 435/212; 435/219
[58] Field of Search .................. 195/62, 66 R; 424/94

[56] References Cited

U.S. PATENT DOCUMENTS 3,409,719  11/1968  Noe et al. .................. 424/94

OTHER PUBLICATIONS

Levenson et al., "Chemical Debridement of Burns" in Annals of Surgery, vol. 180, Oct. 1974, pp. 670–704 (pp. 670, 673, 681,693,696–699, 702–704).

Primary Examiner—Lionel M. Shapiro
Attorney, Agent, or Firm—Cooper, Dunham, Clark, Griffin & Moran

[57] ABSTRACT

Disclosure relates to novel hydrolytic enzyme product derived from the pineapple plant useful for the digestion, dissection and separation of non-viable, devitalized tissue, especially eschar tissue from viable tissue in a mammalian host.

8 Claims, No Drawings

HYDROLYTIC ENZYME MATERIAL

This is a continuation of application Ser. No. 678,695 filed Apr. 20, 1976, now abandoned which is a continuation-in-part of copending application Ser. No. 489,254 filed July 17, 1974 now abandoned, which in turn is a continuation of application Ser. No. 431,622 filed Jan. 8, 1974, now abandoned.

BACKGROUND OF INVENTION

This invention relates to novel hydrolytic enzyme products, therapeutically useful compositions containing such materials, and to methods of utilizing such products especially in debridement of eschar tissue.

Considerable efforts have been made to discover materials capable of distinguishing between viable and non-viable tissue. The discovery of materials which would digest devitalized tissue while not attacking viable tissue would make it possible to remove the devitalized tissue without surgery. It would be a beneficial therapeutic agent in virtually all disease processes where topically devitalized tissue needs to be removed from the viable organism such as decubitus ulcers, pressure necroses, incisional traumatic and pyogenic wounds, and ulcers secondary to peripheral vascular disease.

One area that has attracted considerable attention is the use of proteolytic enzymes and other chemicals to effect the early debridement of eschar tissues resulting from burns. Such devitalized tissue is an excellent culture medium and the principal source of the septicemia which is the proximate cause of death in the majority of severely burned patients. Intensive investigations with such agents as tannic acid, salicylic acid, and pyruvic acid as well as papain, pinguinain, trypsin, streptokinase and other enzymes have not led to satisfactory results. Chemical agents such as tannic acid were found to cause further injury to already damaged tissue. The proteolytic enzymes were found to be too slow, to have toxic side effects or to attack viable as well as devitalized tissue.

It is important that debridement of eschar tissue take place early, i.e. in a period which is preferably no longer than four days, and by an agent which effects debridement rapidly. If debridement is postponed for too extensive a period, there results septicemia from invasion of the wound by infectious microorganisms and toxemia from absorption by viable tissue of toxic degradation products from the devitalized tissue. Rapid debridement is essential since the environment normally encountered is one which serves as an ideal culture media for the growth of infectious colonies of microorganisms.

As a result surgical debridement with its attendant pain and heavy bleeding continues to be the principal method for the removal of eschar.

The enzyme bromelain which is, in fact, a complex mixture containing materials including a number of hydrolytic and proteolytic enzymes has been used in the treatment of burns. In fact, hydrated bromelain powder and some crude extracts of bromelain have been employed previously for debridement of eschar tissue; see Journal of the Maine Medical Association, September 1964; Research in Burns, Hans Huber, Publishers Bern Stuttgart Vienna 1971. These materials, however, have not proved to be satisfactory, principally because the results were not reproducible.

THE INVENTION

Novel hydrolytic enzyme materials useful therapeutically for dissection of devitalized tissues have now been discovered. The novel products of this invention can be employed for dissection and to facilitate removal of devitalized tissue from a mammalian host. The products comprise water soluble, heat labile proteinaceous materials, free of caseinolytic activity. The peak isoelectric point is about 6 and generally ranges from about 5.85 to 6.10. The protein is comprised of at least two and most likely three subunits, each of which has a molecular weight from about 14,300 to 15,000 daltons. There is a characteristic absorption peak in the ultraviolet region of the spectrum at 280 nm. A characteristic of the products of the invention is their hydrolytic activity, even in the absence of sulfhydryl activation or the presence of sulfhydryl deactivating quantities of phenylmercuric acetate. The invention also includes physiologically acceptable alkali metal and acid addition salts of these products. The salts can be prepared by reaction in an aqueous medium between the hydrolytic enzyme substrate and preferably a slight molar excess of the selected dilute alkaline metal base or acid, normally a mineral acid or a low molecular weight aliphatic carboxylic acid. Typically useful bases include sodium and potassium hydroxide. Acids which can be employed include hydrochloric and acetic acids.

The products of this invention may be obtained by appropriate treatment of commercially available bromelain preparations which may be obtained from Castle and Cooke, Inc. of San Francisco, California. In the presently preferred procedure for obtaining bromelain from the stem of the pineapple plant, the juice from the stem is first adjusted to a pH of about 3 or 4 with phosphoric acid and sodium sulfhydride is added to protect against sulfhydryl oxidation. A precipitate is formed by the addition of sufficient acetone so that the solution is 30% in acetone and, after filtration, the clarified fluid is again precipitated by the addition of sufficient acetone so that the fluid is 70% in acetone. This precipitate is collected by centrifugation and either redissolved in water containing sodium sulfhydride which has been acidified with phosphoric acid and reprecipitated, or dried in a vacuum oven directly. If the material is reprecipitated, 70% acetone is utilized. The dried material from either process is suitable as a starting material to obtain the hydrolytic material of this invention.

Either of these source materials is extracted (10 grams per 200 ml.) in acetate buffer 0.1 M, pH 5.5 which has been made up to 1% in thioglycolic acid. The pH of this solution is approximately 4. The solution is expressed through XM 50 Amicon Diaflo ultrafilter (Amicon Corp., Boston, Mass.). This product is an anilsotroic, ultra-filtration, polyacrylic membrane with a molecular weight cut off of about 50,000. The class is described in U.S. Pat. No. 3,615,024.

The macromolecular mixture thus obtained is further purified to obtain the hydrolytic enzyme products of this invention. The mixture is first subjected to molecular exclusion chromatography as a phenylmercuric salt [prepared by combining the mixture with an aqueous 0.2 M citrate buffer saturated with the phenylmercuric acetate salt in accordance with the procedure of Ota et al in Biochem. 3:180 (1960)] on a column of Sephadex G 75. The elution of the desired enzyme product from this column preceded the elution of pure stem bromelain, and therefore must have a molecular weight in excess of bromelain, which is known to be about 32,000.

Sephadex G 75 is a polysaccharide gel available from Pharmacia of Upsala, Sweden. It is employed for molecular exclusion chromatography in accordance with procedures well known in the art.

In further separation and purification experiments the macromolecular mixture was fractionated by isoelectric focusing and subjected to polyacrylamide gel analytical electrophoresis in 1% sodium diodecyl sulfate (SDS).

For isoelectric focusing the mixture was mixed in a sucrose gradient with LKB Ampholine amphalytes initially from pH 3 to 10, and subsequently at pH 5-8. The active material was concentrated at a peak isoelectric point of pH 6.04, with a range from 5.85 to 6.12. This isoelectric point is markedly different from those described for the proteases called bromelain (pH 4.7 and 9.9). See Vestberg Acta. Chem. Scand 20:820 (1966).

LKB Ampholine is available from the LKB Company of Sweden for isoelectric focusing. It is believed to be a mixture of small ampholytes.

The products isolated by isoelectric focusing have an extremely high order of useful hydrolytic activity.

The isoelectric focused active material is in turn subjected to polyacrylamide gel electrophoresis at pH 9 in 1% SDS (Weber et al J. Biol. Chem. 244:4406 (1969). Only one protein staining band can be visualized with a measured electophoretic mobility which, when compared with standard proteins of known molecular weight, evidences a molecular weight of between 14,300 and 15,000 daltons. Since SDS is known to dissociate proteins into their various subunits, if any, it is apparent that the enzyme products of this invention comprise at least two, and most likely three, subunits of substantially the same molecular weight.

The material isolated from isoelectric focusing was subjected to ultraviolet spectrophotometry in water and exhibited a maximum absorption at 280 nm. This absorption is characteristic of aromatic amino acids.

It is concluded, as a result of the foregoing studies, that the products of the invention are proteinaceous in nature and contain aromatic amino acids. They were found to be water soluble and heat labile. While the materials of the invention appear to be substantially pure by the procedures studied, there are most likely small quantities of other materials still present. The activity does not require absolute purity and molecular homogeneity.

The products of the invention, as isolated by isoelectric focusing, were demonstrated to contain no caseinolytic activity when incubated under standard conditions with casein, in accordance with the procedure of Ota et al referred to hereinabove. Bromelain exhibits a high order of caseinolytic activity under these conditions.

The void volume from the G-75 Sephadex column chromatography described above which contained the hydrolytic enzyme product also contained phenylmercuric acetate which inactivates sulfhydryl enzyme. The fact that this enzyme activity occurred in the presence of the mercuric compound indicates that, unlike bromelain, it does not require free sulfhydryl groups for its biological effect. However, it was found that when crude acetone precipitated bromelain was subjected to molecular ultrafiltration in the absence of thioglycolic acid (a sulfhydryl protector), the activity was substantially reduced.

The molecular weight range of the active products in the compositions of this invention is such that pathogenic organisms which are known to be of much higher molecular weight are excluded. The products of the invention therefore are inherently sterile provided, of course, that they are prepared under sterile conditions.

It is clear that the fraction is different from any previously reported materials. Moreover, unlike any previously reported materials it is safe, reliable and effective. The therapeutic results arising from its proper utilization are predictable and reproducible.

While the most active materials of this invention, on a weight basis, are those which are obtained from isoelectric focusing as described above, it is not necessary nor is it practical to carry the purification procedure to this point. The unexpected and most beneficial properties of the products of this invention are obtained with products which are not necessarily so completely purified.

For most purposes, useful products can be provided in two forms. The lyophilized product is generally less dense than the fraction obtained by acetone precipitation. Either fraction can be used alone or in conjunction with the usual pharmaceutically acceptable excipients such as petrolatum, isotonic saline, polysaccharide gels or other stable, inert hydrocarbon bases. Such compositions should be prepared immediately prior to use since the products of the invention are not stable in the presence of moisture.

In certain situations, it may be desirable to add other active ingredients to the therapeutic compositions of the invention. For example, antibiotics may be added to the mixture. These agents or other antimicrobial agents, such as bacitracin, may be useful to control bacteria and fungi and to control possible infection. A keratolytic agent such as urea may be added to aid in the breakup of the eschar tissue.

To determine the biological effects of the products of this invention, experimental full thickness burns were produced on anesthetized piglets by radiant heat. Six different piglets were tested. Each experimental burn was soaked with normal saline for periods of up to four hours after the passage of time indicated in the table below:

Table 1

| Post Burn Period | Duration of Saline Soak |
| --- | --- |
| 1 hour | 0 hour |
| 24 hour | 1 hour |
| 36 hour | 1.5 hour |
| 48 hour | 2 hour |
| 72 hour | 4 hour |

Each burn was punctured with a series of small holes to permit easy passage of the hydrolytic activity through the eschar tissue to the underlying demarcation line between the eschar tissue and the viable tissue. The burns are then separately coated with a powder of the invention and then with agar. The agar is coated with a flexible, plastic sheet, and the edges of the sheet are tightly adhered to the surrounding flesh to protect against the oxygen in the air. A small amount of normal saline is then injected through the plastic and into the agar. This moisture has two effects. It swells the agar to further protect the enzyme from oxygen and it activates the enzyme.

The active powder was applied to the eschar tissue in a quantity of 0.1 mg/mm$^2$. The hydrolytic composition is effective in quantities as low as 0.1 mg/mm$^2$, but is preferably used in quantities up to 10 mg/mm², or even higher to insure contact of the enzyme with the non-viable tissue substrate.

At the end of a one-hour period, the coverings were removed and it was found that the non-viable tissue could be removed from the viable tissue with minimal bleeding and with no apparent toxic effects. The bed of viable tissue remaining after removal of the eschar is suitable for acceptance of a graft.

The graft was applied to the experimental burns from which the eschar tissue was removed after first washing with hydrogen peroxide to neutralize remaining enzymatic activity, and then washing with normal saline. The grafts took successfully.

In a subsequent test with a human subject, a full thickness burn 5 cm² in area was formed on the skin surface of the anterior thigh under local anesthesia by exposure to radiant heat for thirty seconds at 360° Celsius. At the end of one hour, a paste formed from a 1:1 mixture of the powdered product of this invention in physiological saline solution was applied to the burn. The paste was covered with a transparent plastic sheet to seal out oxygen and to maintain humidity, and then with a pressure bandage to secure good contact between the burn substrate and the therapeutic material. The dressing was removed after one hour and the eschar tissue was found to be partially digested. There was no adherence of the wound bed, and the remains of the eschar tissue were completely removed by simple wiping, leaving a wound bed suitable for acceptance of a graft.

It was observed that even after the effects of the local anesthetic had subsided, there was no pain associated with the removal of the partially digested tissue, or any other manipulation of the wound bed. The bleeding was minimal.

The wound bed was covered with a split thickness autograft. The autograft was inspected after four days. It was found that the graft bed was almost fully covered. At the end of seven days, the wound bed was 100% covered with a viable skin autograft.

It has been observed that the active material does not digest the eschar tissue appreciably when exposure is of relatively short duration, for example, one hour. Rather, it dissects the eschar tissue from the underlying tissue by cleaving the connecting tissue. This reaction takes place extremely rapidly.

The rapid dissolution of the connecting tissue was illustrated by another experiment of the nature described above with a piglet having an experimental burn. The entire eschar and the surrounding tissue was covered with an adhesive plastic spray and then a small vertical hole about 1 mm in diameter and 5 mm deep was drilled in the center of the eschar. The hole was filled with a powdered product of the invention and then moistened with a few drops of saline colored with Evans Blue dye. Care was taken so that none of the enzymatic material spilled over the edges of the hole, and it was sealed with plastic. After one hour, bluish discoloration was apparent around the periphery of the burned area (about 2×2 inches). When the plastic seal was removed, it was found that the diameter of the drilled hole had increased to about 10 mm. Furthermore, the eschar tissue could easily be lifted away from the viable tissue with little or no bleeding. This experiment was repeated several times with both lyophilized and acetone precipitated material in undiluted powdered form and in various carriers such as physiological saline, vanishing cream and agar and with substantially identical results.

What has been described are water soluble hydrolytic enzyme compositions containing proteins having a molecular weight of from about 30,000 to 50,000 daltons. It is activated by moisture. However, if exposed to a moist atmosphere for an extended period of time, say for example a day or more, it is subject to autodigestion with loss of activity. The mixture also loses its useful activity when exposed to a temperature of 100° Celsius for about five minutes. It is therefore heat labile.

In still further experiments, four to six weeks old piglets anaesthesized with diethylether were shaved in small areas taking care not to create superficial abrasions. Radiant heat of 360° Celsius applied for twenty seconds with the heat source being an electrically heated rod in an insulated chamber with a variable opening. There was no contact of the heating rod with the skin. The variability of contact pressure was therefore eliminated. The standard assay burn size was two centimeters by five centimeters, with the edges shielded against excess heat by heavy asbestos plate which has to be cooled to room temperature before each new application in order to limit the burn injury to the actual opening in this asbestos plate which also can be varied in size but in standard assay was chosen to be two by five centimeters. This size was chosen in order to channel the efficacy of the active material along a narrow strip of eschar, facilitating at a distance of separation from the injection edge, the actual efficacy of the injected fraction.

One hour after the burn injury, the test fraction was injected at the smaller side of the rectangle (2 cm.), 1 cm. from each corner of the eschar with the needle inserted at the edge of the burn injury and tangentially with the slight 10° angulation advanced parallel to the longer sides of the rectangle about one centimeter into the sub-eschar space. The instrument with which the fraction was injected best was a TB syringe with a 25-gauge short needle. The bevel of the needle was directed towards the viable base during the injection. The amount of test fraction injected was dissolved in 0.1 cc. volume if distilled water. This technique places a pre-measured amount of test fraction dissolved in 0.1 cc. of distilled water in the sub-eschar space one centimeter from each side of one end of the 2×5 cm. rectangle burn.

One hour after the fraction had been placed in the sub-eschar space with the needle left in the injection canal in order to avoid loss of the active material by reflux through the injection canal, the needle was removed and a small rake, 2 centimeters in width with about five teeth sharpened at the point, pushed in a 45° angle into the junction line between eschar and adjacent non-burned tissue along the smaller side of the rectangular burn where one hour before the test fraction had been inserted into the sub-eschar space. Imitating a mechanical separation in an actual burn debridement, the rake was pulled in the direction of the longer axis of the burn wound after the teeth of the rake were engaged in the edge of the eschar. With active fractions it is possible to peel the eschar out of the burn wound leaving a viable slightly bleeding base. The amount of mechanical pull with which the eschar strip can be peeled off this base depends on the loosening or partial softening of the collagen strands with which the eschar is anchored to the wound bed. The ease with which this peeling process can be effective can be measured by a weight attached to the handle of the rake with a fine string lead over a pulley with the animal anchored against a board to which the pulleys are attached. The second measure of the efficacy of the text extract is the distance a nonconstant weight pull is able to peel the eschar strip measured from the edge of the insertion of the rake towards the opposite small edge of the rectangular eschar. Both the pulley weight required to peel off the eschar, and the length in which the eschar strip of 2×5 centimeters can be peeled off along the longer axis of this rectangular burn starting from the smaller border where the test fraction had been injected, demonstrates the efficacy of the particular test fraction in accelerating the demarcation of the heat predetermined plane between irreversibly devitalized eschar and viable wound bed.

Using this technique it has been found that aqueous compositions, particularly physiological saline solutions containing from about 0.1 to 2% by weight of active material can be usefully employed.

What is claimed is:

1. An enzyme product obtainable from bromelain capable of debridement of devitalized tissue from a mammalian host which comprises a water soluble, heat labile protein free of caseinolytic activity having a peak isoelectric point of about 6, comprising at least two subunits, each subunit having a molecular weight of from about 14,300 to 15,000 daltons, with a characteristic absorption peak in the ultraviolet region of the spectrum at 280 nm.; the said product being active in the absence of sulfhydryl activation and in the presence of sulfhydryl deactivating quantities of phenylmercuric acetate, and the physiological acceptable alkali metal and acid addition salts thereof.

2. A pharmaceutical composition comprising a pharmaceutically acceptable excipient together with an enzyme product obtainable from bromelain capable of debridement of devitalized tissue from a mammalian host which comprises a water soluble, heat labile protein, free of caseinolytic activity, having a peak isoelectric point at about 6 comprising at least 2 subunits, each subunit having a molecular weight of from about 14,300 to 15,000 daltons with a characteristic absorbtion peak in the ultraviolet region of the spectrum at 280 nm.; the said enzyme being active in the absence of sulfhydryl activation and in the presence of sulfhydryl deactivating quantities of phenylmercuric acetate, and the physiologically acceptable alkali metal and acid addition salts thereof.

3. A composition as in claim 2 wherein the excipient is physiological saline.

4. A composition as in claim 3 wherein the weight ratio of enzyme product to physiological saline is 1:1.

5. A composition as in claim 2 additionally containing at least one antimicrobial agent.

6. A composition as in claim 2 wherein the excipient is selected from the group consisting of solid polysaccharide gels and solid hydrocarbon bases.

7. A composition as in claim 6 wherein the polysaccharide gel is an agar gel.

8. A composition as in claim 6 wherein the hydrocarbon bases is petrolatum.

* * * * *